United States Patent [19]

Inoue et al.

[11] Patent Number: 4,802,760
[45] Date of Patent: Feb. 7, 1989

[54] RAMAN MICROPROBE APPARATUS FOR DETERMINING CRYSTAL ORIENTATION

[75] Inventors: Yasuo Inoue, Itami; Takeshi Ikeda, Hachioji, both of Japan

[73] Assignee: Mitsubishi Denki Kabushiki Kaisha, Tokyo, Japan

[21] Appl. No.: 143,401

[22] Filed: Jan. 13, 1988

[30] Foreign Application Priority Data

Mar. 25, 1987 [JP] Japan .................................. 62-72247

[51] Int. Cl.$^4$ ......................... G01J 3/44; G01N 21/65
[52] U.S. Cl. ....................................... 356/31; 356/301
[58] Field of Search ................................ 356/31, 301

[56] References Cited

FOREIGN PATENT DOCUMENTS

| 2594227 | 8/1987 | France ............................... 356/301 |
| 17032 | 1/1986 | Japan ................................. 356/301 |
| 2186363 | 8/1987 | United Kingdom ................ 356/301 |

OTHER PUBLICATIONS

Journal of Applied Physics, "Raman Microprobe Determination of Local Crystal Orientation", by J. B. Hopkins et al, pp. 1103–1110, Feb. 15, 1986.

Primary Examiner—F. L. Evans
Attorney, Agent, or Firm—Lowe, Price, LeBlanc, Becker & Shur

[57] ABSTRACT

A Raman microprobe apparatus for determining crystal orientation comprises a polarizer for polarizing not only incident light but also Raman light. The polarizer is provided between a half mirror for deflecting the incident light toward a specimen and an object lens system for focusing the incident light on the specimen.

2 Claims, 2 Drawing Sheets

RAMAN MICROPROBE APPARATUS FOR DETERMINING CRYSTAL ORIENTATION

CROSS-REFERENCE TO RELATED, COPENDING APPLICATION

Related, copending applications of particular interest to the instant application are U.S. Ser. No. 011,329 filed Feb. 5, 1987 and U.S. Ser. No. 011,511 filed Feb. 6, 1987 both assigned to the same assignee of the instant application.

BACKGROUND OF THE INVENTION

1. Field of the Invention

The present invention relates to a Raman microprobe apparatus for determining crystal orientation by utilizing polarization selective Raman microprobe spectroscopy, and more particularly to improvements in simplicity and accuracy of the apparatus.

2. Description of the Prior Art

Raman microprobe determination of cyrstal orientation is described, e.g., in J. Appl. Phys., Vol. 59, 1986, pp. 1103-1110 by J. B. Hopkins et al.

Referring to FIG. 1, there is schematically illustrated an arrangement of a principal portion in a conventional Raman microprobe apparatus for determining crystal orientation. An incident beam 1a of circularly polarized light is converted into a linearly polarized light beam 1b by a polarizer 7 which can be rotated. The linearly polarized light beam 1b is deflected by a half mirror 5 and then a light beam 1c thus deflected is focused on a specimen 4 by an object lens system 3.

Raman light scattered from the specimen 4 is collected as a Raman light beam 2a by the object lens system 3, a half of which is transmitted as a beam 2b through the half mirror 5 and then deflected as a beam 2c toward a polarization analyzer 8 by a complete mirror 6. A Raman light beam 2d having a particular polarization plane is selected from the beam 2c by the polarization analyzer 8.

The polarization-selected Raman light beam 2d is then introduced into a spectrometer (not shown) and then the Raman band of the specimen 4 is measured. In the conventional apparatus, the polarization intensity characteristic of the selected Raman light 2d is measured with either the polarizer 7 or polarization analyzer 8 being fixed and the other being rotated by degrees. The measured data of the polarization intensity characteristic are processed by a computer and compared with data derived theoretically as to known crystal orientation, whereby the crystal orientation of the specimen 4 can be determined.

In the conventional apparatus, however, it is difficult to make correction for a measured data which contains experimental errors due to polarization plane shifts and light intensity distribution changes at the half mirror 5 and complete mirror 6.

In FIG. 1, linearly polarized light 1b having a particular polarization angle is selected by the polarization 7 from circularly polarized incident light 1a. This linearly polarized light 1b is reflected by the half mirror 5 and then slightly changes to linearly polarized light 1c having a polarization angle and intensity distribution both shifted a little from those of the light 1b. As well known, the reason is that the reflectance of a mirror changes depending on the polarization angle of light. Since the Raman scattering is excited by the polarized light 1c slightly different from the polarized light 1b, it is necessary to make correction as to an error in the measured data which is caused by the difference between the light 1b and the light 1c.

When Raman light 2a is transmitted through the half mirror 5, it also changes to light 2b having slightly different polarization components and slightly different intensity distribution. Further, when the light 2b is reflected by the complete mirror 6, it slightly changes to light 2c. A polarization angle and intensity distribution of linearly polarized light 2d selected from the light 2c are slightly different from those of the Raman light just as scattered from the specimen 4. Therefore, it is also necessary to make correction as to errors in the measured data which is caused by the polarization angle shifts and intensity distribution changes in the Raman light at the half mirror 5 and the complete mirror 6.

As described above, it is necessary in the conventional apparatus to make correction for the measured data as to the polarization shifts in both the incident light and Raman light. However, since it is difficult to separate the errors in the obtained data due to the respective polarization shifts in the incident light and the Raman light, it is compelled to make averaged correction. Therefore, some error still remains in the corrected data, and the accurate value can not be known.

Further, since the measurements are carried out with either the polarizer 7 or polarization analyzer 8 being rotated and the other being fixed in the conventional apparatus, not only the two optical parts of the polarizer and analyzer but also a parameter representing the analyzer relation between the polarizer and analyzer is indispensable.

SUMMARY OF THE INVENTION

In view of the prior art, it is an object of the present invention to provide a Raman microprobe apparatus for determining crystal orientation, in which it is not needed in the measured data to take into consideration the polarization shifts at the half mirror and complete mirror.

It is another object of the present invention to provided a Raman microprobe apparatus for determining crystal orientation, in which not only the number of optical parts but also the number of parameters in analyzing data is decreased by providing a polarizer which functions not only as the prior art polarizer but also as the prior art analyzer.

According to the present invention, a Raman microprobe apparatus for determining crystal orientation comprises a half mirror for deflecting circularly polarized incident light toward a specimen, a polarizer for selecting linearly polarized incident light from the deflected incident light, and an object lens system for focusing the linearly polarized incident light onto the specimen, wherein Raman light scattered from the specimen is collected as a Raman light beam by the object lens system and linearly polarized by the polarizer before it is transmitted through the half mirror.

Namely, the circularly polarized incident light is converted by the polarizer into the linearly polarized incident light after deflected by the half mirror and just before focused on the specimen by the object lens system. Therefore, there is no shift between the intended polarization angle and practical polarization angle in the incident light focused on the specimen.

Meanwhile, just after the scattered Raman light is collected by the object lens system and before the collected Raman light is transmitted through the half mirror, linearly polarized Raman light having the intended polarization angle is selected by the polarizer from the collected Raman light. Therefore, the practically measured Raman light corresponds directly to that having the intended polarization angle.

Further, since the polarization polarizes not only the incident light but also the Raman light, the linearly polarized Raman light to be measured has the completely same polarization angle as that of the linearly polarized incident light. In other words, there is not needed a parameter representing the polarization angular relation between the linearly polarized incident light and linearly polarized Raman light.

These objects and other objects, features, aspects and advantages of the present invention will become more apparent from the following detailed description of the present invention when taken in conjunction with the accompanying drawings.

DESCRIPTION OF THE PREFERRED EMBODIMENTS

Figure 2:
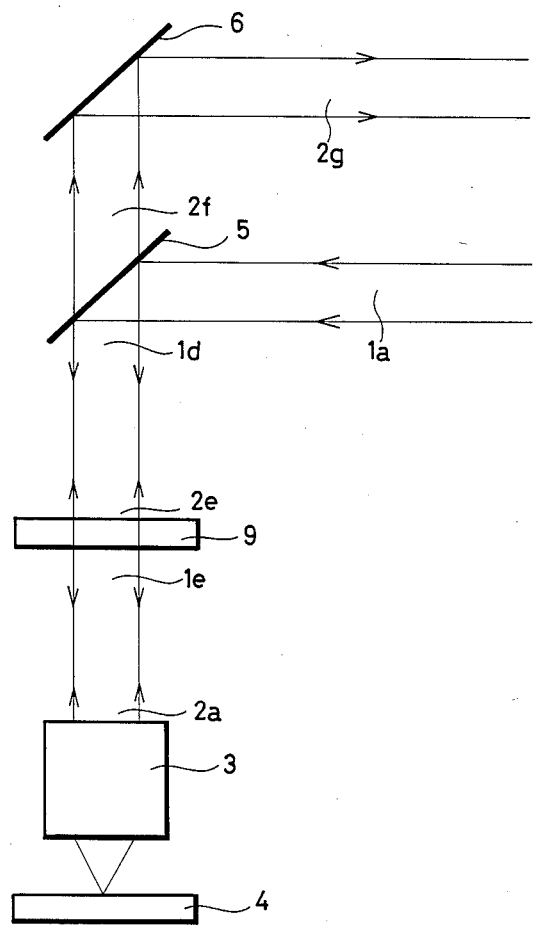
FIG. 2 is a schematic diagram illustrating an optical system in a principal portion of a Raman microprobe apparatus for determining crystal orientation according to an embodiment of the present invention.

Referring to FIG. 2, when circularly polarized incident light 1a is deflected by a half mirror 5, it changes to a little elliptically polarized incident light 1d. Linearly polarized light 1e having a particular polarization plane is selected from the light 1d by a polarizer 9 and then focused on a specimen by an object lens system 3. Raman light scattered from the specimen 4 is collected as a Raman light beam 2a by the object lens system 3. Linearly polarized Raman light 2e having the same polarization plane as that of the incident light 1e is selected from the Raman light 2a by the polarizer 9. When the linearly polarized Raman light 2e is transmitted through the half mirror 5, it changes to light 2f having a slightly changed polarization direction and slightly changed intensity distribution. Similarly, when the Raman light 2f is deflected by the complete mirror 6, it changes to light 2g having a further slightly changed polarization direction and further slightly changed intensity distribution. Then, the linearly polarized Raman light 2g is introduced into a spectrometer (not shown). In the spectrometer, the Raman bands of the specimen 4 are separated and the light intensity is measured with respect to various polarization planes. The measured data of the polarization characteristic in the Raman light is compared with that derived theoretically as to known crystal orientation, whereby the crystal orientation of the specimen 4 can be determined.

In the apparatus of FIG. 2, as described above, the polarization angle of the incident light is selected just before the incident light is focused on the specimen and then the polarization angle of the Raman light is selected just after the Raman light is collected from the specimen. Therefore, it is not necessary to take into consideration the shifts of the polarization angle at the half mirror 5 and complete mirror 6, and it is necessary only to make correction as to the measured light intensity. In this case, once data for the intensity correction are prepared, they do not change during the measurements. Therefore, the light intensity can be measured, precisely corresponding to the polarization angle in the incident light and the Raman light.

Figure 1:
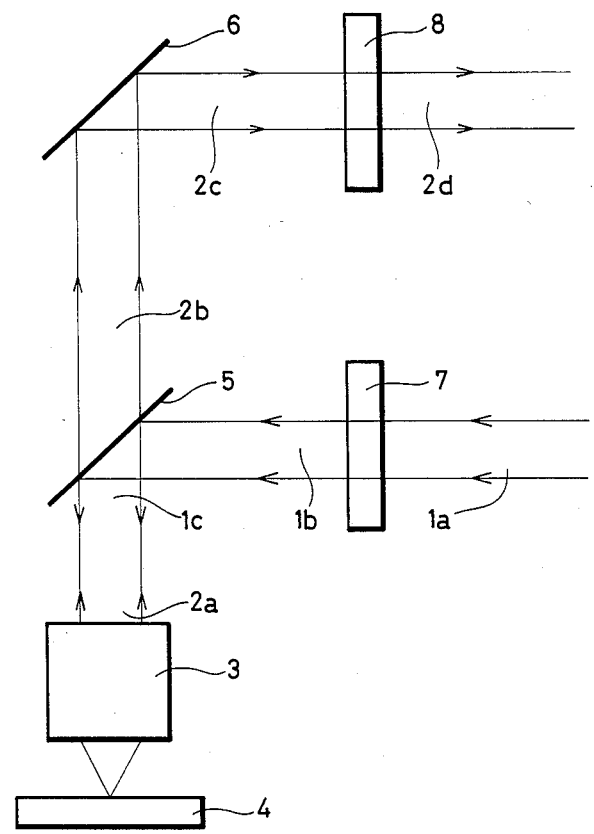
FIG. 1 is a schematic diagram illustrating an optical system in a principal portion of a conventional Raman microprobe apparatus for determining crystal orientation.

Further, since the polarizer 9 in FIG. 2 functions not only as the prior art polarizer 7 for the incident light but also as the prior art analyzer 8 for the Raman light, the number of the optical parts is decreased by one. Accordingly, although the parameter representing the angular relation between the polarizer 7 and analyzer 8 is necessary in analyzing the data measured with the conventional apparatus of FIG. 1, such a parameter is not necessary with the apparatus of FIG. 2.

Although the polarizer 9 was provided between the half mirror 5 and the object lens system 3 in the above described embodiment, it may be provided in the object lens system 3 or between the object lens system 3 and specimen 4. In this case, however, the performance of the polarizer is reduced a little, because convergent incident light and divergent Raman light are introduced into the polarizer.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A Raman microprobe apparatus for determining crystal orientation, comprising:
   a half mirror for deflecting circularly polarized incident light toward a specimen,
   a polarizer for selecting linearly polarized incident light from the defected incident light, and
   an object lens system for focusing the linearly polarized incident light onto the specimen,
   wherein Raman light scattered from the specimen is collected as a Raman light beam by the object lens system and linearly polarized by the polarizer before it is transmitted through the half mirror.

2. A Raman microprobe apparatus in accordance with claim 1, further comprising a complete mirror for deflecting the Raman light toward a spectrometer after the Raman light is transmitted through the half mirror.

* * * * *

UNITED STATES PATENT AND TRADEMARK OFFICE
CERTIFICATE OF CORRECTION

PATENT NO. : 4,802,760

DATED : February 7, 1989

INVENTOR(S) : Yasuo INOUE et al.

It is certified that error appears in the above-identified patent and that said Letters Patent is hereby corrected as shown below:

Under [73] Assignee (title page), add second named assignee as follows:

Japan Spectroscopic Co., Ltd.

Signed and Sealed this

Twenty-fifth Day of July, 1989

Attest:

DONALD J. QUIGG

Attesting Officer

Commissioner of Patents and Trademarks